United States Patent [19]

Sandel et al.

[11] Patent Number: 4,674,676

[45] Date of Patent: Jun. 23, 1987

[54] CLOSABLE, DISPOSABLE, FOLDUP CONTAINER FOR USED MEDICAL MATERIALS

[75] Inventors: Dan Sandel; Mike Hoftman, both of Northridge, Calif.

[73] Assignee: Devon Industries, Inc., Chatsworth, Calif.

[21] Appl. No.: 794,683

[22] Filed: Nov. 4, 1985

[51] Int. Cl.⁴ .............................................. B65D 5/24
[52] U.S. Cl. .................................... 229/142; 206/366;
206/438; 229/149; 229/150; 229/174; 229/186;
229/45 R
[58] Field of Search ................... 229/31 R, 31 FS, 24,
229/25, 26, 44 R, 45 R, 39 R, 186, 188, 142,
149, 150, 174; 206/363, 366, 620, 438, 807;
220/1 T

[56] References Cited

U.S. PATENT DOCUMENTS

| | | | |
|---|---|---|---|
| 1,061,531 | 5/1913 | Emmons | 229/31 R |
| 1,307,638 | 6/1919 | Pridham | 229/31 R |
| 1,328,935 | 1/1920 | Wade | 229/39 R |
| 1,341,429 | 5/1920 | Lewis | 229/45 R |
| 1,985,111 | 12/1934 | Shofer et al. | 229/188 |
| 2,364,267 | 12/1944 | Battery | 229/186 |
| 2,536,948 | 1/1951 | Lehman | 229/31 FS |
| 2,682,988 | 7/1954 | Rosen et al. | 229/31 R |
| 2,950,850 | 8/1960 | Corcoran | 229/26 |
| 3,542,569 | 11/1970 | Farquhar | 229/31 R |
| 4,121,755 | 10/1978 | Meseke et al. | 206/366 |
| 4,315,592 | 2/1982 | Smith | 206/366 |
| 4,534,489 | 8/1985 | Bartlett | 229/45 R |

FOREIGN PATENT DOCUMENTS

| | | | |
|---|---|---|---|
| 1501985 | 10/1967 | France | 229/44 R |
| 696547 | 9/1953 | United Kingdom | 229/39 R |
| 896921 | 5/1962 | United Kingdom | 229/31 R |

*Primary Examiner*—William Price
*Assistant Examiner*—Gary E. Elkins
*Attorney, Agent, or Firm*—Poms, Smith, Lande & Rose

[57] ABSTRACT

An inexpensive, foldup container for holding and disposing of used medical materials is die-stamped from a single piece of cardboard material and crimped along a plurality of lines to define a plurality of rectangular panels hingably-attached to one another which fold together to form a rectangular carton having an aperture in the top guarded by a barrier flap which permits the one-way disposal of used medical materials, such as disposable sharps and dressings, and further includes a hinged cover which can be locked shut over the disposal opening to retain the contents within the container and to resist tampering during the disposal process. The container may be provided in a partially assembled, flat configuration for storing and shipping.

3 Claims, 9 Drawing Figures

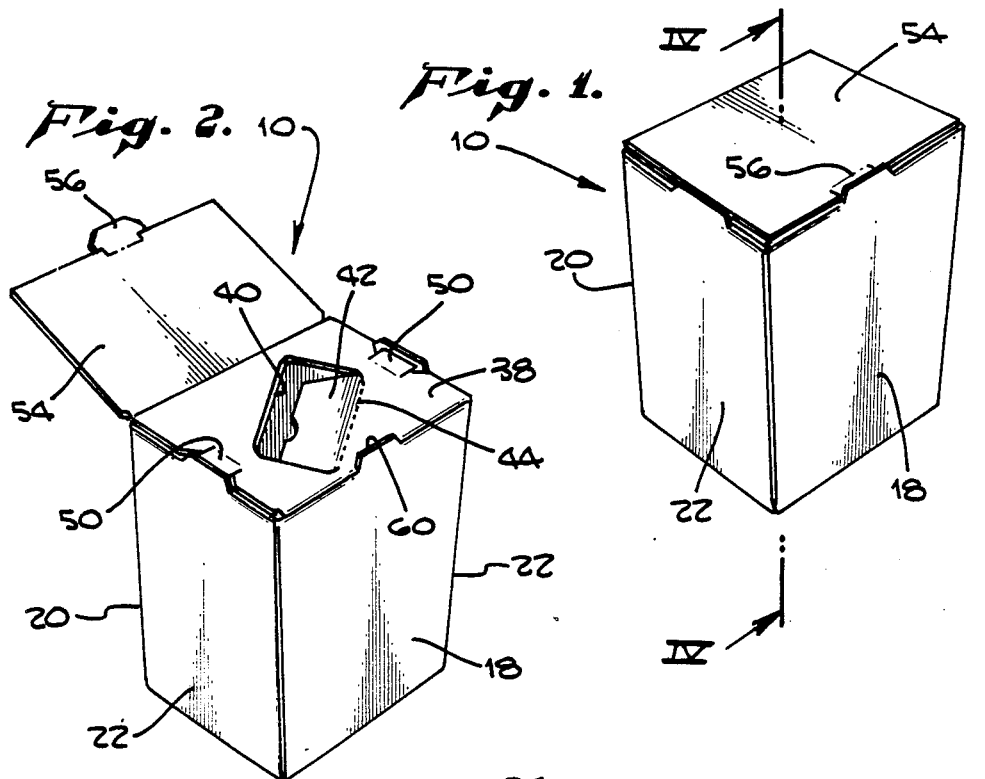
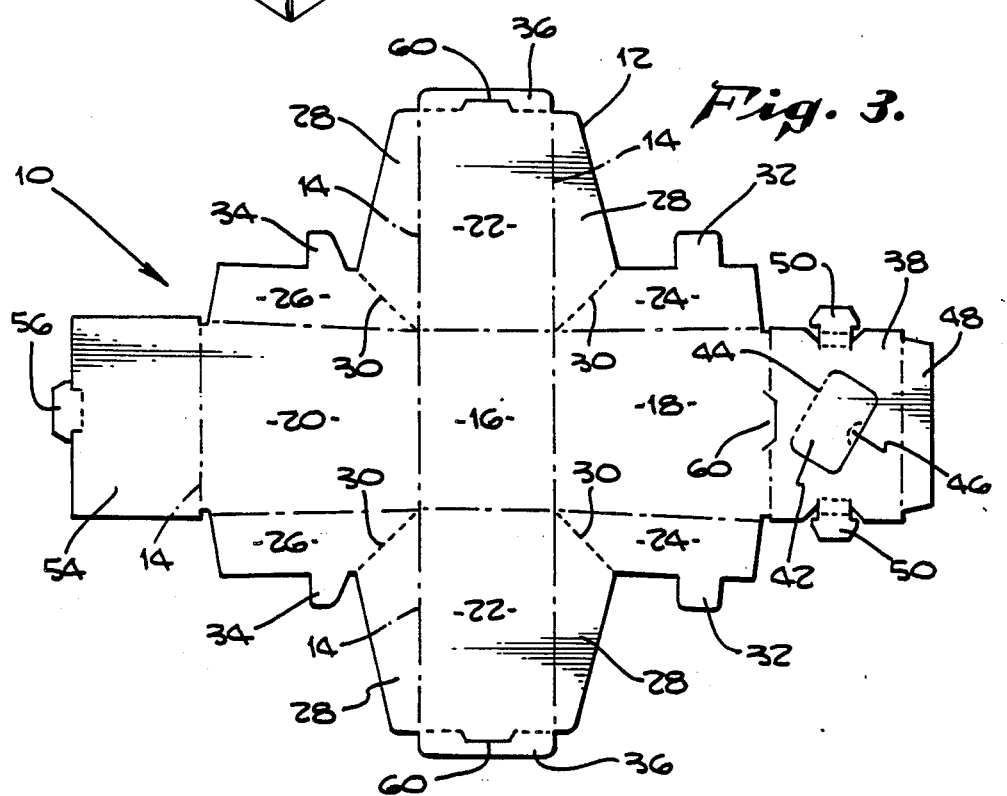

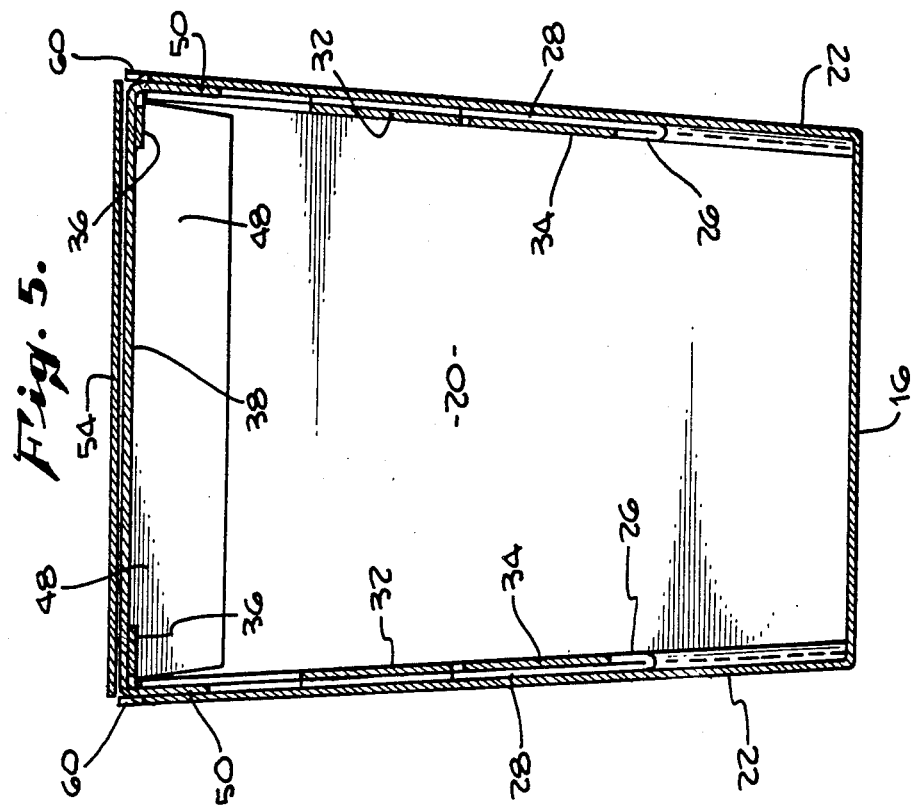
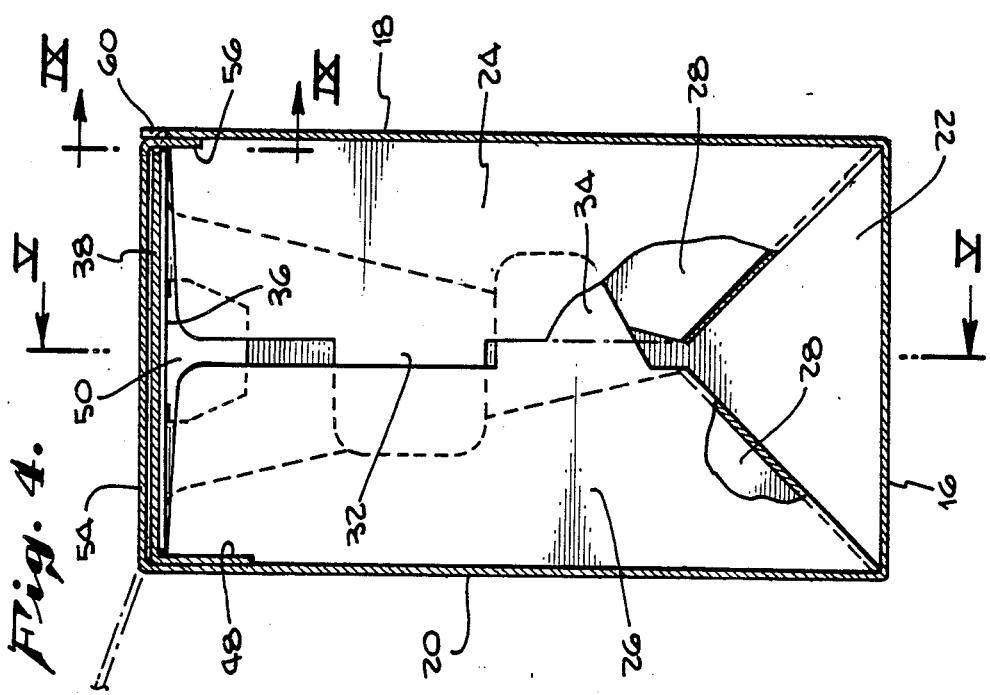

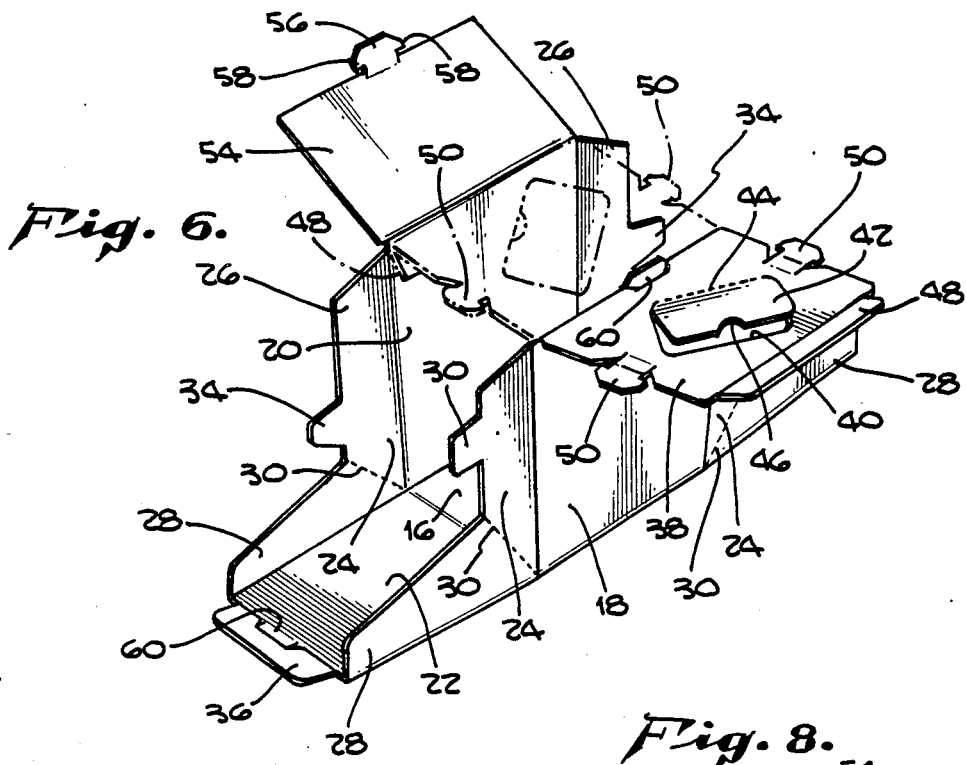

CLOSABLE, DISPOSABLE, FOLDUP CONTAINER FOR USED MEDICAL MATERIALS

BACKGROUND OF THE INVENTION

1. Field of the Invention

This invention relates, in general, to medical-surgical supplies for hospitals, infirmaries, doctors' offices and the like, and more particularly to a foldup, disposable container having a closure for holding and disposing of used medical-surgical materials, including "sharps," e.g. hypodermic needles, suture needles and scalpel blades.

2. Summary of the Prior Art

This decade has seen an acceleration of the trend in the field of medical care provision of the use of disposable, one-time-use medical-surgical devices and materials. This trend is away from the former procedure of sterilization and re-use of these devices, both for reasons of expense and sterility.

Present hospital protocol in those institutions employing the use-and-dispose philosophy entails the assembly and distribution by unskilled personnel of clean, but not sterilized, flexible plastic or paper containers to those locations where containment is required, e.g., operating rooms, nurses' stations, soiled linen rooms and emergency rooms, or so-called "med/surg" rooms, i.e., those where simple, out-patient surgery is performed.

The containers are then used by medical personnel to contain used medical-surgical materials, e.g., used hypodermic syringes, needles, dressings, cotton applicators, etc., until the containers become filled, at which time they are collected by unskilled housekeeping personnel for disposal. In some states, this involves processing of the used materials by incineration, and in some states, by law, the materials are "red-bagged" or boxed, and stored for pick-up by contract disposal personnel. The containers of materials to be disposed may then be autoclaved under low-pressure steam to sterilize them, then buried in a landfill.

During the containment and disposal procedure, it is desirable that the person using the containers be protected from direct contact from infectious materials with which the used medical materials may be contaminated. Moreover, it is also desirable to protect personnel from contact with so-called "sharps" i.e., those materials capable of causing wounding injury, such as hypodermic needles or scalpels. Regarding the latter, it is also desirable that the containers present a relatively tamper-resistant barrier against the casual scavenger intent on procuring hypodermic needles and/or syringes for illicit purposes.

Various types of disposable containers having been developed heretofore for use in disposal, counting and/or containment of used medical materials, such as in my prior U.S. Pats. Nos. 4,013,109 and 4,418,821, and such as is described in my pending patent application, Ser. No. 838,296, filed on Mar. 10, 1986, and entitled, "A Rigid, Disposable Container for Holding and Disposing of Used Medical Sharps and Other Medical/Surgical Materials."

I have found that it would be desirable to provide a more inexpensive, simpler disposable container for holding and disposing of used medical materials, which folds flat for storage and can be folded up by relatively unskilled labor to form the desired container, while yet retaining the above-described desirable attributes.

SUMMARY OF THE INVENTION

It is therefore a primary object of the present invention to disclose and provide a disposable, closable, foldup container for holding and disposing of used medical materials which is inexpensive and capable of being folded to a flat arrangement for storage before use.

These objects are preferably accomplished in a container comprising a flat, profiled cutout from a sheet of semi-rigid material which is compression-crimped along a plurality of lines to define a plurality of panels hingably attached to each other along the crimp lines to fold and lock together to form the rigid container, the container having a closed top with a rectangular aperture therethrough for placement of used medical materials into the container, the aperture being about the size of an average hand and being guarded by a one-way barrier flap which is hingably attached to the top of the container, the barrier flap being perforated along its hinge lines to permit the flap to be easily removed, the container further being provided with a folding closure panel which is hinged to the container to fold foward over the top and the disposal opening and lock with the container by means of a locking tab, which serves to retain the material within the container during the disposal procedure and to provide a degree of tamper resistance to the closed container.

A more complete understanding of the present invention will be had by those skilled in the art, as well as an appreciation of an additional advantages and objects therefrom, by a consideration of the following detailed description of a preferred exemplary embodiment thereof and reference to the appended sheets of drawings, the following of which is a brief description.

BRIEF DESCRIPTION OF THE DRAWINGS

FIG. 1 is a perspective view of a preferred embodiment of the present invention, a closable, disposable, foldup container for holding and disposing of used medical materials, in which the cover is shown in the shut and locked position;

FIG. 2 is a perspective view of the container illustrated in FIG. 1 in which the cover is shown in the opened position, revealing the rectangular disposal aperture and the one-way barrier protecting it;

FIG. 3 is a plan view of a profiled cutout of which the preferred embodiment of the container is constructed;

FIG. 4 is a cross section through the side of the container, as revealed by the Section IV—IV taken in FIG. 1;

FIG. 5 is a cross section through the front of the container of the present invention, as revealed by the Section V—V taken in FIG. 4;

FIG. 6 is a perspective view of the container of the present invention in a partially-folded and assembled configuration;

FIG. 7 is a partial-sectional view through the locking tab detail of the container of the present invention in which the locking tab is shown in two positions relative to the container;

FIG. 8 is a partial detail of the locking aperture of the container, as revealed by the Section VII—VII taken in FIG. 7.

FIG. 9 is a partial-sectional view through the locking tab and top panel of the container, as revealed by the Section IX—IX taken in FIG. 4.

DETAILED DESCRIPTION OF A PREFERRED EMBODIMENT

FIGS. 1 and 2 illustrate an assembled, exemplary preferred embodiment of the present invention, a closable, disposable, foldup container for used medical materials 10. FIG. 1 illustrates container 10 with the closure cover 54 locked in place, whereas FIG. 2 illustrates container 10 in the open configuration with closure cover 54 hinged backwards to permit access to disposal opening 40.

A more complete understanding of the construction and assembly of container 10 may be had from a consideration of FIGS. 3 and 6. FIG. 3 and 6. FIG. 3 illustrates the container 10 in a flat, completely unfolded plan view. In the exemplary embodiment, container 10 comprises a single sheet 12 of flat material having an outer periphery as illustrated. Preferably, sheet 12 is die-stamped stamped from a larger piece of sheet stock which, in the preferred embodiment, comprises conventional or corrugated cardboard container stock, i.e., two layers of paper stock arranged in a parallel fashion, having opposing surfaces joined by a third layer of corrugated stock which is bonded to the opposing layers at the crests and troughs of the corrugations.

This applicant has had very good results in forming inexpensive, lightweight, yet rugged containers from ordinary corrugated cardboard carton stock. However, the container of the present invention may also be easily fabricated from a variety of other sheet stock materials, including single-layer cardboard stock and foam-core, depending upon the application. Similarly, it is to be noted that an enhanced moisture resistance in the container at a slightly increased production cost may be obtained from use of a sheet stock in which one or both sides of the sheet stock have been coated or impregnated with a moisture-resistant material, such as a clear plastic or paraffin.

Returning to FIG. 3, the single sheet 12 contains a plurality of crimp lines 14 which are impression stamped into sheet 12 and which may be accomplished simultaneously with the die-stamping operation. Crimp lines 14 are formed by a local displacement of one surface of sheet 12 toward the other, and serve to define a plurality of panels for the container and to reduce the stiffness of the material locally between the panels to permit ease of folding of the panels relative to one another along the crimp lines, in the manner of a hinged attachment.

The plurality of panels defined by the crimp line 14 include a bottom panel 16, a front panel 18, a rear panel 20 and a pair of side panels 22. Side panels 22 additionally are each hingably attached to front panel 18 along one side edge by a pair of pleated gusset panel pairs 24 and 28, which, in turn, are hingably attached to one another along a crimp line 30 which intersects bottom panel 16 between side panel 22 and front panel 18. A similar arrangement attaches side panel 22 at its other side edge to rear panel 20 through gusset panel pairs 26 and 28.

Adjacent panels 24 and 26 each have formed thereon an interleaving tab 32 and 34, respectively, the purpose of which is to interleave with an opposing gusset pair to retain the folded gusset panel pairs against the side panels 22 when container 10 is in the folded-up configuration.

Attached to side panels 22 are a pair of hinged closure flaps 36, which, in the assembled container 10, assist in holding side panels 22 in place.

Hingably-attached to front panel 18 along its top edge is top panel 38. In the exemplary embodiment illustrated, the top panel 38 includes a rectangular disposal opening 40 which is created by partially cutting a rectangle into top panel 38 to leave a barrier flap 42 hingably-attached along one edge to top panel 38 to serve as a one-way barrier through which used medical materials may be disposed into container 10. In the preferred embodiment, rectangular aperture 40 is about the width and heighth of an average hand. It is intended in using container 10 of the present invention that the user of the container not be required to place any part of the hand through disposal opening 40 in order to dispose of used medical materials, and that barrier flap 42, in conjunction with top panel 38, serve as a one-way barrier against escape of contaminated materials from container 10 and/or infectious contact of using personnel with the contents therein. However, in some applications, it may be desirable to remove barrier flap 42 entirely from the container to permit ease of disposal of materials. To that end, the exemplary embodiment of container 10 contains a plurality of perforations 44 along the barrier flap 42 hinge line to permit the flap 42 to be torn away with ease by the user, if desired. To facilitate grasping of the barrier flap 42, a finger notch 46 is die-cut into the panel.

Top panel 38 also includes an assembly flap 48 hingably attached at its outer edge, as well as a pair of locking tabs 50 disposed on either of its sides.

Hingably attached to rear panel 20 is a closure cover 54, including a locking tab 56 disposed on its outer edge.

The configuration and operation of locking tabs 50 and 56 are best understood by reference to FIGS. 7–9. Representative of locking tabs 50, locking tab 56 includes a pair of locking ears 58 disposed on either side of the tab. To accommodate the locking tabs 50 and 56, side panels 22 and front panel 18 each are stamped to contain a locking aperture 60, located along the upper edge of the respective panels at a crimp line 14. When container 10 is in the folded-up configuration, locking apertures 60 are open to receive locking tabs 50 and/or 56 such that the tabs penetrate into the container and locking ears 58 engage the underside of their receiving panels to prevent the locking tabs from being disengaged. Thus, it is impossible to withdraw locking tabs 50 or 56 without destroying the tabs.

A more complete understanding of the assembly procedure for the exemplary container 10 may be had by reference to FIGS. 5–6. Container 10 is assembled by folding each of front panel 18, rear panel 20 and side panels 22 upwardly relative to bottom panel 16. Pleated gusset panel pairs 24 and 28 and 26 and 28 are folded along hinged line 30 such that the gusset panels fold inward upon themselves and lie parallel against the inside surface of side panels 22. Interleaving tabs 32 and 34 are engaged between the panels of the opposing gusset-panel pair to retain the gusset panels against the inside surface of side panels 22, thus providing corner seams in container 10 which are leak resistant and tamper resistant, and which also lend structural rigidity to the assembly (see FIG. 4). Top panel closure flap 48 tucks down into container 10 in front of rear panel 20 and between the edges of side panel closure flaps 36. Side panel closure flaps 36 tuck beneath the top panel 38 to form a closed container. Cover panel locking tabs 50 are then inserted into their respective locking apertures 60 to complete the assembly of the container 10. Barrier panel 42 is then pressed inwardly into container 10 to provide access for disposal of used medical materials therein. When container 10 is filled, the closure cover 54 is simply folded forward over top panel 38 to cover disposal opening 40 and lock tab 56 is inserted in its respective locking aperture 60 to seal the container 10 for disposal.

In the exemplary embodiment illustrated, top panel closure flap 48 is adhesively-attached to rear panel 20 before the container is delivered to the user. Ths forms an open-ended rectangular tube which may be collapsed at diagonal corners for flat storage and shipping to the user, while simplifying the assembly process for the user at the time of assembly.

By now, it will be understood by those skilled in the art that various modifications and alterations thereof may be made to the preferred exemplary embodiment of the present invention illustrated and discussed herein. For example, it will be obvious to those skilled in the art that a wide variety of sizes and shapes of container may be obtained by a simple variation of the geometry of the stamping or cutting procedure and the impression-stamping process used to define the hingably-attached panels. Accordingly, the scope of and spirit of the instant invention, a closable, disposable foldup container for used medical materials, should be limited only by the following claims.

I claim:

1. A closable, foldup container for holding and disposing of used medical materials, comprising:

a flat profiled cut-out consisting of a single piece of semi-rigid sheet material, said cut-out being compression crimped along a plurality of lines to define edges of a plurality of panels therein, hingably-attached to each other along said crimp lines, said panels including a bottom panel, a front panel, a rear panel, two side panels, a top panel, a closure panel and a plurality of gusset panels, said front, rear and side panels each having a top edge, a bottom edge and a pair of side edges, each said bottom edge being hingably-attached along one of said crimp lines to an edge of said bottom panel for folding upward thereabout, each said panel side edge meeting an adjacent said panel side edge when upstanding to define four vertical corners of said container, each said gusset panel being hingably-attached along one of said crimp lines to one of said side edges of each of said front, rear and side panels and to an adjacent said gusset panel along an intermediate one of said crimp lines, such that each pair of said adjacent gusset panels folds together inwardly along said intermediate crimp line and lies flat against one of said side panels when said front, rear and side panels are folded upwardly together for vertically reinforcing said container and sealing said container's vertical corners, one of said gusset panels in each said gusset panel pair having a tab for interleaving between the opposing said gusset panel pair when said container is folded up, for holding said gusset panels against said side panels, said top panel having a front edge, a rear edge and a pair of said edges, said top panel front edge being hingably-attached along one of said crimp lines of said front panel top edge to fold back over said side panel top edges, each said side panel having a closure flap hingably-attached along one of said crimp lines to said side panel's upper edge to tuck beneath said top panel, said top panel having a closure flap hingably-attached along one of said crimp lines at said top panel's rear edge to tuck down between said side panel closure flaps and said rear panel, said top panel closure flap having an outer surface adhesively-attached to an adjacent inner surface of said rear panel before said side panels are folded up, for provision of said container in a partially-assembled, flat condition, each said top panel side edge having a locking tab thereon for insertion into said container, each said side panel closure flap having a locking aperture therethrough at said side panel upper edge to receive one of said locking tabs, for holding said container upstanding when said container is folded up, said top panel being cut through along a closed profile except for a portion consisting of a straight line to define a disposal aperture through said top panel guarded by a barrier flap hingably-attached to said top panel along said straight line within said aperture, to permit said barrier flap to hinge inwardly into said container and disposal of said used medical materials through said aperture into said container, said closure panel having a front edge, a rear edge, and a pair of side edges, said rear edge being hingably-attached along one of said crimp lines to said rear panel upper edge to fold forward over said top panel to cover said disposal aperture and close said container for disposal, said closure panel front edge having a locking tab thereon for insertion into said container to lock said closure panel in place for resistance to tampering, said top panel having a locking aperture therethrough at said front panel upper edge to receive said closure panel locking tab, to hold said closure panel closed.

2. The container of claim 1, wherein:

said sheet of semi-rigid material is coated on at least one side with a coating from the following group: wax and clear plastic.

3. The container of claim 1, wherein:

said barrier flap hinge line contains a plurality of perforations to permit said barrier flap to be selectively torn away.

* * * * *